Figure 1:
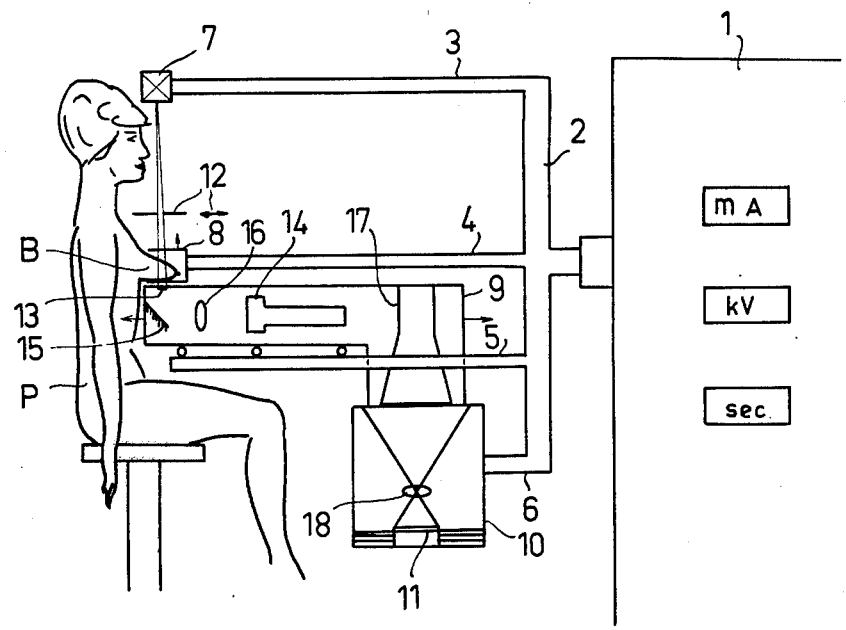

United States Patent [19]

Geluk

[11] 4,020,347
[45] Apr. 26, 1977

[54] MAMMOGRAPHY

[75] Inventor: Ronald Jan Geluk, Nootdorp, Netherlands

[73] Assignee: N.V. Optische Industrie de Oude Delft, Delft, Netherlands

[22] Filed: Mar. 29, 1976

[21] Appl. No.: 671,378

[30] Foreign Application Priority Data

Apr. 1, 1975  Netherlands .................. 7503862

[52] U.S. Cl. .................. 250/361 R; 178/DIG. 5; 250/363 R; 250/416 TV
[51] Int. Cl.² .................. A61B 6/00; G01T 1/20
[58] Field of Search .............. 178/DIG. 5; 250/369, 250/358, 363 S, 363 R, 361, 362, 320, 323, 416 TV

[56] References Cited

UNITED STATES PATENTS

| | | | |
|---|---|---|---|
| 2,730,566 | 1/1956 | Bartow et al. | 250/363 |
| 3,101,407 | 8/1963 | Shipman, Jr. | 250/363 |
| 3,790,799 | 2/1974 | Stein et al. | 250/363 |
| R28,544 | 9/1975 | Stein et al. | 250/369 |

Primary Examiner—Alfred E. Smith
Assistant Examiner—T. N. Grigsby
Attorney, Agent, or Firm—O'Brien & Marks

[57] ABSTRACT

Method and apparatus for detecting and recording breast cancer, in which the breast is exposed to X-rays, preferably in the so-called soft range, the transmitted beam of rays is scanned by means of a moving, strip-shaped screen and the image of the strip-shaped screen is picked up with a television pickup tube moving along with the screen, and is displayed on a monitor tube.

11 Claims, 2 Drawing Figures

U.S. Patent

April 26, 1977

4,020,347

MAMMOGRAPHY

This invention relates to a method and apparatus for detecting and recording breast cancer by means of X-rays, the so-called mammography.

It is very important to detect breast cancer in a very early stage in order to minimize the consequences for the person afflicted. To this effect there has been developed a technique for photographing the breast by means of X-rays, in which it is possible to detect minute details and very low contrasts by means of a specially constructed X-ray source. Thus breast cancer or embryonal breast cancer can be detected in a very early stage.

However, a objectionable side effect is that the radiation dose to which the person to be examined is exposed is not negligibly small. As a result, there is a remote chance that such mammographic examination has detrimental effect on the patient's health.

Some researchers estimate that the number of induced carcinomas is 1 in 10,000 at an absorbed radiation dose of 1 Rad per photo and 6 photos per examination. In case of a large scale examination this may lead to an appreciable number of carcinomas caused by the examination.

The above shows that it is desirable to employ an examination method that is simple and reliable and which minimizes the required radiation dose.

According to the present invention there is provided a method of detecting and recording breast cancer characterized in that the breast is exposed to X-rays, the beam of transmitted rays is scanned by means of a moving strip-shaped screen, and the image of said screen is picked up by a television pickup tube moving there along and displayed on a monitor tube.

According to a further elaboration of the principle of the present invention the above described method is further characterized in that the stripshaped screen and the television pickup tube are continuously moved.

An apparatus for applying the method according to the invention is characterized by a stationary source of X-rays; an X-ray permeable breast support surface; a frame movable underneath the surface and carrying a strip-shaped screen arranged to scan the X-ray beam through the movement of the frame, said frame further carrying an optical system and a television pickup tube; a monitor tube; and a magazine for a photographic film on which the images of the monitor tube can be successively recorded for producing a total image, the film and the monitor tube being relatively movable.

Further embodiments of the essence of the invention will be described in the following.

The invention will now be described, by way of example, with reference to the accompanying drawings, wherein FIG. 1 shows an embodiment of an apparatus according to the invention.

Figure 2:
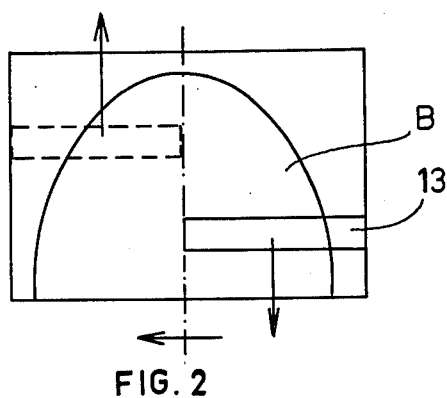

FIG. 2 shows the manner in which the breast is preferably scanned.

FIG. 1 shows a console 1 comprising power-supply and control means for the apparatus according to the invention. Console 1 is provided with a carrier 2 having four arms 3,4,5,6. The uppermost arm 3 carries a suitable X-ray source 7 providing preferably soft X-rays. The second arm 4 is provided at the end with a support member 8 for the breast being examined. Said support member may consist of a simple X-ray permeable surface or of a breast enclosing box, open at least at one side, as shown.

The third arm 5 forms a track for a frame 9 to be described hereinafter. Finally the fourth arm 6 carries a magazine 10 for a photographic film 11 on which the resultant image can be recorded.

Furthermore there is depicted a patient P, to illustrate the manner in which the mammographic examination can be performed. Between the X-ray source and the breast to be examined there may be positioned a slotted diaphragm 12, as will be described hereinafter.

The frame 9 may suitably be controlled by control means mounted in the console or possibly by hand so that it is capable of rolling or sliding over arm 5, during which operation a screen 13 mounted on the frame is moved to underneath the support member 8 and thus underneath the patient's breast.

The screen 13a is a known per se screen which is adapted for converting impinging X-ray quanta into light quanta. The light quanta produced by the screen form a representation of the X-ray shadow image of the breast being examined. For reproducing this, use is made according to the invention of a television circuit. Thus the light quanta are captured by means of a highly sensitive television pickup camera 14 and visualized by a monitor tube 17. For this purpose, in the embodiment shown, there is mounted underneath the screen 13 a mirror 15 adapted to aim the light at a lens system 16 ensuring the proper size of the image so that it can be processed by the television camera 14. The television camera is positioned on the frame 9 and consequently follows the movement of the screen 13.

An isocon camera which can be advantageously employed as the camera 14 has a photocathode as detector having a quant yield of about 20%. Thus it is possible in principle, by means of a lens system with e.g. 5% photon capture, to develop a mammography apparatus enabling a radiation dose a few times smaller than that of known apparatus.

In the realization of an apparatus according to the principles of the present invention, some difficulties of a practical nature occur which result from the fact that the photocathode of e.g. a 2 inch isocon has an image width of only 36mm. As a result the lens system should have a reduction factor of approximately 5 so that the desired 5% photon capture could not be attained. Moreover the contrast transfer of a television circuit is limited to about 400 lp/image width, while a transfer of 800 lp/image width is required for enabling a reliable breast examination.

These two problems are solved according to the present invention by virtue of the image being composed of a number of portions by means of an objective having a reduction factor of 2.5.

FIG. 2 shows the manner in which the image is preferably built up. For this purpose the screen 13 is strip-shaped and the frame 9, as already described, can be so controlled that the screen 13 scans the X-ray beam along two parallel, contiguous paths. By passing the screen 13 in two parallel movements underneath the breast B, as shown by the arrows in FIG. 2, it is possible, through application of a lens system having a reduction factor of 2.5 to obtain a total horizontal resolution about 2 times as high as that which would be obtained in case the total width is represented.

Because the part to be scanned is each time limited to a narrow strip of e.g. 90 x 10 mm, it is possible to obtain a corresponding resolution in vertical direction as well if the vertical deflection is adapted to the strip height.

In order to minimize the radiation dose for the patient, there is positioned between the X-ray source and the patient a slotted diaphragm 12 moving along with the screen. This diaphragm limits the primary radiation to the area covered by the screen 13.

This has the additional advantage that the stray radiation is greatly suppressed, which is not possible in the mammography systems hitherto known.

The thus obtained strip-shaped images are successively displayed on a monitor tube 17 which executes the same movement as the screen 13 and the camera 14 because the monitor tube is likewise attached to the frame 9.

The image on the monitor may be directly observed but is preferably recorded on a photographic film 11 by means of suitable optical means 18. The film does not move and preferably has dimensions such that successively all strip-shaped images, which together form a total image of the breast, can be integrated on the film to one image. In principle it is also possible to maintain the monitor tube in a fixed position while causing the film to execute the required translations.

The movement of frame 9 and hence of screen 13, camera 14 and monitor 17 can take place both by increments and in a continuous manner. Continuous scanning offers the advantage that defects in the screen 13 will be motion-blurred on the film with a resultant lower contrast, so that the risk of confusion with a detected carcinoma or an embryonal carcinoma is small.

Summarizing, it can be stated that the use of a television circuit with strip-shaped scanning for the purpose of carrying out a breast examination, offers the following advantages:

1. the required radiation dose is a few times smaller than in known systems;
2. through the use of a moving slotted diaphragm stray radiation is suppressed, which results in higher contrast;
3. there is a possibility of controlling the speed of the image buildup, thereby allowing the X-ray dose to be adapted in situ to the breast to be examined; as a result there is achieved, in addition to a more harmonious image, a still smaller radiation dose for the patient;
4. structural noise of the X-ray screen, of the camera and of the monitor is substantially suppressed;
5. various forms of contour accentuation and image harmonization are possible by reversing the polarity of the video signal for a number of line times;
6. gamma correction by electronic means may be utilized;
7. since the monitor tube 17 can provide a very bright image, it is possible to employ low-sensitivity film material having a large density range and a fine grain;
8. the recording process can be followed with an additional monitor and, if need be, can be restarted; in practice this may mean a reduced radiation dose for the patient.

Furthermore it is possible to mount, in the radiation transmitted through the slotted diaphragm, an X-ray filter which transmits over a first part of its surface the relatively hard radiation, and over a second part of its surface all impinging radiation. By means of corresponding display with positive and negative polarity, it is now possible to obtain artificially an image that seems to have been produced by exclusively soft radiation through which contrast in the object can be better visualized. For the same purpose use can be made in the display section of the apparatus of different colour filets on the reproduced strip, the recording being effected on colour film, whether or not in combination with the X-ray filter.

Finally it is observed that, although the invention has been described with particular reference to mammography, other parts of the body can be examined by the same principle and the same apparatus, and so can other types of objects requiring a minimal radiation dose, or in which the amount of radiation passed by the object is small.

I claim

1. A method of detecting and recording breast cancer, wherein a breast is exposed to X-rays, the transmitted beam of rays is scanned by a moving strip-shaped screen and the image of the strip-shaped screen is picked up by a television pickup tube moving along with the screen and displayed on a monitor tube.

2. A method according to claim 1, wherein the strip-shaped screen and the television pickup tube are moved continuously.

3. A method according to claim 1, wherein the strip-shaped screen and the television pickup tube are moved stepwise.

4. A method according to claim 1, wherein the monitor tube is moved in the same manner as the pickup tube and the screen, the monitor image being recorded on a stationary film.

5. A method according to claim 4, wherein the film is moved relatively to the monitor tube for forming a total image.

6. A method according to claim 1, wherein the X-rays are focussed at the breast through a slotted diaphragm moving in correspondence with the movement of the screen.

7. A method according to claim 1, wherein the period of time during which each object part is recorded is adapted instantaneously to the local physical build-up of the breast to be examined.

8. Method according to claim 6, wherein there is mounted in the radiation transmitted through the slotted diaphragm an X-ray filter which, over a part of the diaphragm surface, exclusively transmits relatively hard radiation.

9. A method according to claim 1, wherein colour filters are mounted on the monitor tube window and that recording takes place on colour film.

10. Apparatus for detecting and recording breast cancer, characterized by a stationary X-ray source; an X-ray permeable support surface for the breast to be examined; a frame adapted for movement underneath the support surface and which carries a strip- shaped screen by means of which the beam of X-rays can be scanned through the movement of the frame, said frame also carrying an optical system and a television pickup tube; a monitor tube; and a magazine for a photographic film whereon the images of the monitor tube can be successively recorded for providing a total image, the film and the monitor tube being relatively movable.

11. Apparatus according to claim 10, characterized by a slotted diaphragm disposed between the X-ray source and the breast, said diaphragm being movable in correspondence with the movement of the strip-shaped screen.

* * * * *